United States Patent
Heuer

(10) Patent No.: US 12,310,630 B2
(45) Date of Patent: May 27, 2025

(54) BLADE-LIKE OSTEOSYNTHESIS DEVICE

(71) Applicant: MIMEO MEDICAL GmbH, Filderstadt (DE)

(72) Inventor: Frank Heuer, Filderstadt (DE)

(73) Assignee: MIMEO MEDICAL GmbH, Filderstadt (DE)

( * ) Notice: Subject to any disclaimer, the term of this patent is extended or adjusted under 35 U.S.C. 154(b) by 198 days.

(21) Appl. No.: 18/015,448

(22) PCT Filed: Jul. 9, 2021

(86) PCT No.: PCT/EP2021/069206
§ 371 (c)(1),
(2) Date: Jan. 10, 2023

(87) PCT Pub. No.: WO2022/013109
PCT Pub. Date: Jan. 20, 2022

(65) Prior Publication Data
US 2023/0277221 A1    Sep. 7, 2023

(30) Foreign Application Priority Data
Jul. 11, 2020 (DE) ............... 10 2020 004 184.1

(51) Int. Cl.
*A61B 17/70* (2006.01)
(52) U.S. Cl.
CPC .................. *A61B 17/7032* (2013.01)
(58) Field of Classification Search
CPC ............. A61B 17/8625; A61B 17/864; A61B 2017/8655; A61B 17/8685; A61B 17/7032–17/704
See application file for complete search history.

(56) References Cited

U.S. PATENT DOCUMENTS 6,063,090 A   5/2000   Schläpfer
6,409,730 B1 * 6/2002  Green .................. A61B 17/74
                                                606/325

(Continued)

FOREIGN PATENT DOCUMENTS

DE   10 2019 000 965   8/2020
JP   2004-513757 A     5/2004

(Continued)

OTHER PUBLICATIONS

International Search Report with English Translation for PCT/EP2021/069206, mailed Nov. 18, 2021, 6 pages.

(Continued)

*Primary Examiner* — Julianna N Harvey
(74) *Attorney, Agent, or Firm* — Nixon & Vanderhye P.C.

(57) ABSTRACT

An osteosynthesis device for the fixation of bone components and bone fragments is disclosed including a bone anchor having a shaft which extends along a central axis and thereby defines a distal and a proximal direction, and includes at least one blade area with a first and a second wing, and proximally adjoins a neck area and further has a head with at least one spherical segment, and the bone anchor has a central and continuous cannula opening with a diameter. The blade area at least one window with an opening width is provided. The window interacts with the cannula opening, and the head area has an opening with an opening diameter, which also interacts with the cannula opening. The diameter of the cannula opening is smaller than the opening width of the window and the diameter of the cannula opening is also smaller than the opening diameter at the head and the shaft is formed in one piece with the blade area, the neck area and the head with spherical segment.

32 Claims, 10 Drawing Sheets

(56) References Cited

U.S. PATENT DOCUMENTS

| | | | |
|---|---|---|---|
| 9,125,696 B2 * | 9/2015 | Linke | A61B 17/74 |
| 9,936,983 B2 * | 4/2018 | Mesiwala | A61B 17/7055 |
| 11,369,419 B2 * | 6/2022 | Mesiwala | A61F 2/44 |
| 2004/0068258 A1 * | 4/2004 | Schlapfer | A61B 17/8625 606/311 |
| 2006/0217717 A1 * | 9/2006 | Whipple | A61B 17/686 606/279 |
| 2010/0331895 A1 * | 12/2010 | Linke | A61B 17/74 606/301 |
| 2011/0098747 A1 * | 4/2011 | Donner | A61B 17/7044 606/264 |
| 2012/0226318 A1 * | 9/2012 | Wenger | A61B 17/7001 606/279 |
| 2014/0066991 A1 * | 3/2014 | Marik | A61B 17/8625 606/279 |
| 2017/0119447 A1 | 5/2017 | Wenger et al. | |
| 2020/0222088 A1 * | 7/2020 | Kraus | A61B 17/7098 |
| 2021/0113250 A1 * | 4/2021 | Major | A61B 17/8685 |
| 2021/0244455 A1 * | 8/2021 | Castro | A61B 17/7035 |
| 2022/0087724 A1 * | 3/2022 | Schlenker | A61B 17/8625 |

FOREIGN PATENT DOCUMENTS

| | | |
|---|---|---|
| WO | 02/45606 | 6/2002 |
| WO | 2020/160722 | 8/2020 |

OTHER PUBLICATIONS

Written Opinion of the ISA for PCT/EP2021/069206, mailed Nov. 18, 2021, 8 pages.

\* cited by examiner

BLADE-LIKE OSTEOSYNTHESIS DEVICE

CROSS REFERENCE TO RELATED APPLICATIONS

The present application is a National Phase of International Application Number PCT/EP2021/069206 filed Jul. 9, 2021, which designated the U.S. and claims priority benefits from German Patent Application Number DE 10 2020 004 184.1 filed Jul. 11, 2020, the entire contents of each of which are hereby incorporated by reference.

STATE OF THE ART

Blade-like implants are used in particular when, in the case of a weakened bone structure, a screw offers too little support or the bone fragments would twist if a screw were used. This is particularly the case with osteoporotic bone tissue. A blade-like implant has a larger surface area than a bone screw and can therefore provide greater stability, mainly with respect to bending loads. However, pull-out forces are only partially tolerated by blades. In this respect, bone screws always have an advantage.

Structurally weakened bony structures are especially often symptomatic in the spine. A bony structure with the highest load-bearing capacity is the cortical pedicle. Therefore, it is desired to provide a blade-like implant for use in the spine, which is supported with the large surface in the cancellous vertebral body area and can additionally be anchored in or on the cortical pedicle.

U.S. Pat. No. 9,125,696B2 discloses a combination of a blade with a bone screw that combines the mechanical advantages of a blade and a bone screw. The implant disclosed in U.S. Pat. No. 9,125,696B2 is designed for general orthopedics and is not suitable for insertion into the pedicle. The prior art includes pedicle screws (U.S. Pat. No. 6,063,090A) that allow polyaxial adjustment of the implant head relative to the bone anchor. This requires at least one spherical segment on the bone anchor head, which is not obvious from the solution presented in U.S. Pat. No. 9,125,696B2. Furthermore, the blade is designed in a straight line without twisting of the wing areas, so that use in the pedicle does not make sense. In the final position in the pedicle, the distal area of the blade in the vertebral body would be on edge with respect to the load direction. Twisting or crossing of the blade surfaces is therefore a biomechanical requirement so that bending loads can be absorbed at the distal implant area within the vertebral body.

WO0245606A1 discloses a twisted blade-like implant for the treatment of the spine. In an embodiment, the combination with a so-called transport screw is presented, which is provided in a window within the blade area. The disclosure lacks essential details in the embodiment with transport screw, which would be necessary for the realization of a functioning structure. Structural aspects necessary to ensure sufficient fatigue strength against recurrent bending loads were also not considered. A window for the transport screw weakens the structural integrity of the blade, so a greatly reduced fatigue strength can be assumed for this design. Similarly, WO0245606A1 discloses a design form with a spherical segment in the head region for use with a polyaxial implant head. However, the technical embodiment of a version with a spherical segment in the head and a functioning transport screw is not shown, since the intended connecting units of the sphere and transport screw are mutually exclusive and impede a joint assembly. The osteosynthesis device according to the invention is intended to solve this problem.

REPRESENTATION OF THE INVENTION

According to the invention presented here, all biomechanically important aspects can be combinatorially and functionally mapped. On the one hand, a blade-like bone anchor with twisted blade surfaces is provided, which has at least one spherical segment at the head area, and on the other hand, this blade-like bone anchor has an internal threaded bush with bone thread. The threaded bush is not only used as a transport screw, but mainly serves to provide pull-out strength for the osteosynthesis device. The threaded bush is located in a rather proximal area of the blade, so that the threaded bush with its bone thread is engaged with the cortical pedicle area. Preferably, the threaded bush is connected to the shaft or blade area by means of a coupling element.

The main loads acting on the osteosynthesis device can be divided into two main components; axial forces and bending loads. The blade area is able to absorb the bending loads and the threaded bush the corresponding pull-out forces. The bending loads are mainly absorbed by the shank with the blades. The bending load increases from distal to proximal and is transferred from the interior of the vertebra to the shaft via the ball to the implant tulip head. It is therefore desired to provide a mechanically optimized connection between the spherical segment and the blade area of the bone anchor. A one-piece structure or a one-piece connection between the ball and the blade area is therefore a biomechanical requirement. The prior art does not disclose a comparable structure for this purpose. Optionally, an intermediate neck area may be provided to allow pivoting with a polyaxial tulip head. A missing neck area would limit the freedom of movement.

To increase the fatigue strength at the highly loaded transition from the blade area, via the neck area to the spherical segment, it is preferable to reduce the distance between the wing top edges at the proximal blade area, so that the wing top edges to the neck area run into the shaft. In addition to improving stability, this also ensures that the osteosynthesis device can be swiveled as soon as it is mounted with a polyaxial tulip head. With differently shaped wing top edges at the proximal transition area, the wing top edges with the polyaxial tulip head would create an impingement and prevent or at least restrict angular deflection. At the same time, it is preferable for the shaft to enlarge towards the neck area at the proximal blade area.

Another option for increasing fatigue strength is to balance the missing structure in the blade area, namely the window for the threaded bush. This can be achieved by the wings having one or more thickenings extending parallel along the central axis of the shaft at least in sections and bridging at least the area of the window. The highest bending stiffness of the blade is achieved when these thickenings are located at the wing top edges. This has the additional advantage that the wing top edges with their thickenings do not cut into the cortical bone in the pedicle region. From an anatomical point of view, the pedicle does not have a concentric contour, but approximately an oval. It is therefore advantageous if the thickenings at the top edges correspond to an oval at least in sections, in order to enable an optimum contact surface between the blade area and the pedicle region. This prevents the blade from cutting into the cortical bone of the pedicle, which is equivalent to optimized load transfer. An additional way to increase the fatigue strength of the osteosynthesis device is to increase the material thickness of the wing areas from distal to proximal.

In order for the osteosynthesis device to be able to absorb pull-out forces, the threaded bush must have at least one suitable area that is in contact with an area of the blade area and can simultaneously absorb a force in axial direction along the central axis. These contact areas are preferably arranged within the window and represent a mechanical stop for the threaded bush. Optimally, a total of two such mechanical stops, one in distal and one in proximal direction, are provided on the threaded bush. Starting from the polyaxial tulip head, for example, an axial tensile force is applied to the osteosynthesis device and, due to the one-piece connection between head and blade, to the blade area. As mentioned above, at least one mechanical stop exists between the blade area and the threaded bush. Due to this stop, the axial tensile force is transferred from the bone anchor to the threaded bush. The bone thread of the threaded bush is in direct engagement with the cortical pedicle bone and thus transmits the initially introduced axial force to the bone. If two mechanical stops are provided in this design, a bidirectional effect against axially introduced tensile or compressive forces is also achieved.

The threaded bush is mounted rotationally within the window in the blade area. The threaded bush is held stationary with the aid of the coupling element. The coupling element is designed to be pluggable so that the threaded bush is held in the window of the blade area by inserting the coupling element into the shaft and through the threaded bush. In addition, the plug-in function has the advantage that a minimum axial movement is allowed in relation to the coupling element when the threaded bush is subjected to an axial load, since the aforementioned stops between the window areas and the threaded bush ensure the load transfer of the axial forces. Thus, the coupling element is not overloaded in axial direction or is even decoupled from the axial load. A minimum relative movement within the stops may be necessary due to manufacturing tolerances of the window and the threaded bush.

The threaded bush is able to rotate independently of the blade area. This is made possible by the fact that the coupling element is in contact with the threaded bush in such a way that a torque can be transmitted from the coupling element to the threaded bush. For this purpose, profiles are used which are in contact with each other, and which are suitable for transmitting a torque and at the same time can be plugged into each other. These include all load-transmitting profiles known from the state of the art, such as flat profiles (e.g. single-flat, double-flat, . . . , hexagonal, . . . , polygonal) or tooth profiles such as Torx. Alternatively, other joining methods are available, such as gluing, pinning, welding, pressing, etc. For the initiation of a torque via the coupling element, it is preferable if the coupling element has a tool attachment point, for which any insert or attachment known from the state of the art can be used. For ensuring self-tapping characteristics of the threaded bush, it is preferable for the external bone thread to have so-called cutting edges. Optimally, they are designed in such a way that when the blade area is driven into the bone, the thread begins to grip in the bone. To reduce the number of turns of the threaded bush, it is preferable for the thread to be double- or multi-start. A single-start version is not excluded.

As already mentioned, the coupling element can be plugged into the shaft and the threaded bush. To ensure that the coupling element is held securely in the shaft, an optional locking mechanism is provided between the coupling element and the shaft. Assembling the osteosynthesis device is quite simple by plugging the components together. Of course, other connection and securing mechanisms are also possible.

If the head of the coupling element protrudes beyond the spherical diameter of the spherical segment, the fixed angle clamping of the polyaxial tulip head can even block the rotation of the coupling element and the threaded bush. If the tulip head is loosened again, this blockage is released.

To further increase the flexural strength of the blade area, it is preferable if the coupling element is mounted in the shaft in the proximal area and extends through the threaded bush and also protrudes distally from the threaded bush and is also mounted in the blade area distal to the window. As a result, there is an additional element in the shaft which can absorb a bending load. This bridges the gap in the window from the inside and increases the bending stiffness. It can also be helpful if the window has an optional web which is an additional strut in the window and thus provides additional bending stiffness of the shaft.

Special dimensional relationships are important to comply with, since an actually functioning assembly of the internal threaded bush, the blade-like bone anchor and the pluggable coupling element should be achieved. A head with spherical segment must be provided, which forms a mechanical unity with the blade area; the bone anchor. Furthermore, there is a window for the threaded bush in the blade area. This already creates a geometrical configuration which can only be released if different specifications and relationships to each other are complied with in accordance with the claims of the invention.

When looking at the anatomy of the spine from the frontal plane, it can be seen that the posterior structures, namely the pedicles, approximate an oval in section and the oval has a centroid axis. In the posterior-anterior sectional view of the pedicle structures, it can be seen that this oval centroid axis changes its orientation angle, and does so differently on the left and right, i.e., in opposite directions. It is therefore necessary to know the crossing direction of the wing torsion of the blade area so that the osteosynthesis device can be inserted anatomically correctly into the corresponding pedicle.

Therefore, it is important to strictly differentiate between a left and a right version of the osteosynthesis device, as these differ in the direction of the wing crossing. Only this difference and a corresponding marking or label, such as "R" for right or "L" for left, can get the biomechanical maximum out of the invention potential. In the worst case, an incorrect combination can lead to a breakthrough of the pedicle wall during implantation.

Naturally, the pedicle channels have a certain form factor, which defines the oval. This form factor defines the relationship between height and width. Optimally, the osteosynthesis devices according to the invention are precisely adapted to this so that they best reflect the oval cross-section. Here, the osteosynthesis device, with the two wings (15, 16) having a width (1516) defined between the top edges of the wings (154, 164) and an outer diameter (252) of the bone thread, has a form factor with the ratio of 1516/252, which is between 1.3 to 2.5, preferably 1.4 to 2.2, preferably 1.6 to 2.0.

As an additional means of increasing anchorage stability in the bone, if the bone quality is too low, a cannula with lateral openings is provided. Bone cement can be injected through these openings. Here it is preferable that the orientation of the lateral openings after implantation always points cranially and caudally, where the greatest load within the cancellous bone is directed. Furthermore, it is advantageous if the central cannula has different diameters to prevent cement from escaping distally.

The tulip head consists of a U-shaped fork head in side view, which has two fork legs with an internal thread in proximal direction, and in which the connecting rod can be accommodated, and a grub screw is guided in the internal thread, and the fork head is detachably connected to the osteosynthesis device. Furthermore, the osteosynthesis device is pivotably mounted in the spherical seat of the fork head, whereby the fork head is designed at the spherical seat area in such a way that the osteosynthesis device is mounted with its spherical segment coming from the distal side.

The osteosynthesis device should be implanted with the wing orientation of the distal end of the bone anchor corresponding to the main orientation of the pedicle canal. This corresponds almost to a cranial-caudal alignment. The osteosynthesis device is driven into the pedicle canal up to the level of the threaded bush by short strikes. As soon as the threaded bush is in contact with the bone, a torque is applied via the tool attachment point of the coupling element, which leads to rotation and thus to driving of the threaded bush in the bone. This transports the osteosynthesis device into the vertebral body. During the entire implantation process, the bone anchoring element rotates around the central axis according to the defined crossing of the wing areas in the blade area. In the final position, the distal wing orientation has a lateral-medial orientation, whereas the proximal wing orientation corresponds to the main pedicle orientation.

BRIEF DESCRIPTION OF THE DRAWINGS SHOW

FIG. 1 the osteosynthesis device according to the invention in an oblique view.

FIG. 2 the sole bone anchor of the osteosynthesis device according to the invention in a side view and with various sectional views. For reasons of better visualization, the twisting of the wings has been omitted.

FIG. 3 shows an exploded view of the osteosynthesis device of FIG. 1.

FIG. 4 the threaded bush with inserted coupling element without the bone anchor.

FIG. 5: Side view and Sectional view of the complete osteosynthesis device according to the invention. Again, the wings have not been twisted for visual reasons.

FIG. 6 an alternative embodiment in which the latch is provided at the head portion.

FIG. 7 the osteosynthesis device according to the invention in another oblique view.

FIG. 8. an alternative embodiment with additional web and two threaded bushes in the window to increase stiffness.

DESCRIPTION

Figure 1:
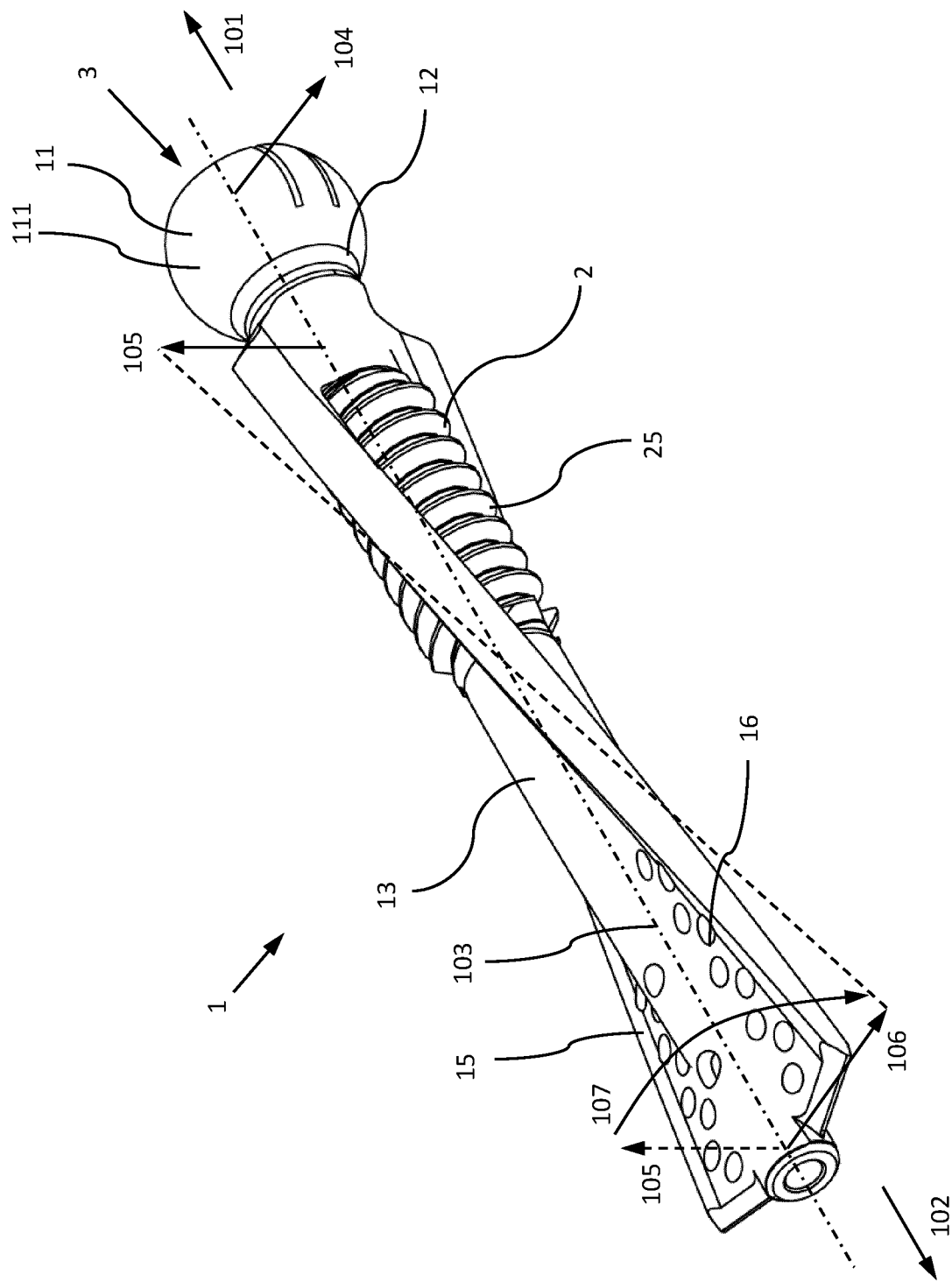

For the osteosynthesis device (10), space-allocating coordinate references are defined, such as the proximal direction (101), the distal direction (102), which extend along a central axis (103). The radial propagation (104) is defined extending outward from the central axis (103). The circumferential spread is defined by a constant radius and along a variable circumferential angle (FIG. 1). The osteosynthesis device (10) is mainly intended for the fixation of bone components and bone fragments, in particular vertebrae. It comprises a bone anchor (1), and this bone anchor (1) comprises a shaft (13) which extends along the central axis (103) and thereby defines a distal (102) and a proximal (101) direction. The bone anchor (1) has at least one blade area (14) with a first (15) and a second wing (16), and is proximally (101) adjacent to a neck area (12) and further to a head (11) with at least one spherical segment (111). An essential feature according to the invention is that the shaft (13) is formed in one piece with the blade area (14), the neck area (12) and the head (11) with spherical segment (111). The osteosynthesis device (10) is further characterized in that the blade area (14), with the two wings (15, 16) at the proximal area (101), has a first wing orientation (105) and the wings (15, 16) at the distal end (102) have a second wing orientation (106) which is different from the first wing orientation (105), this difference being determinable by means of a crossing angle (107).

Figure 2:
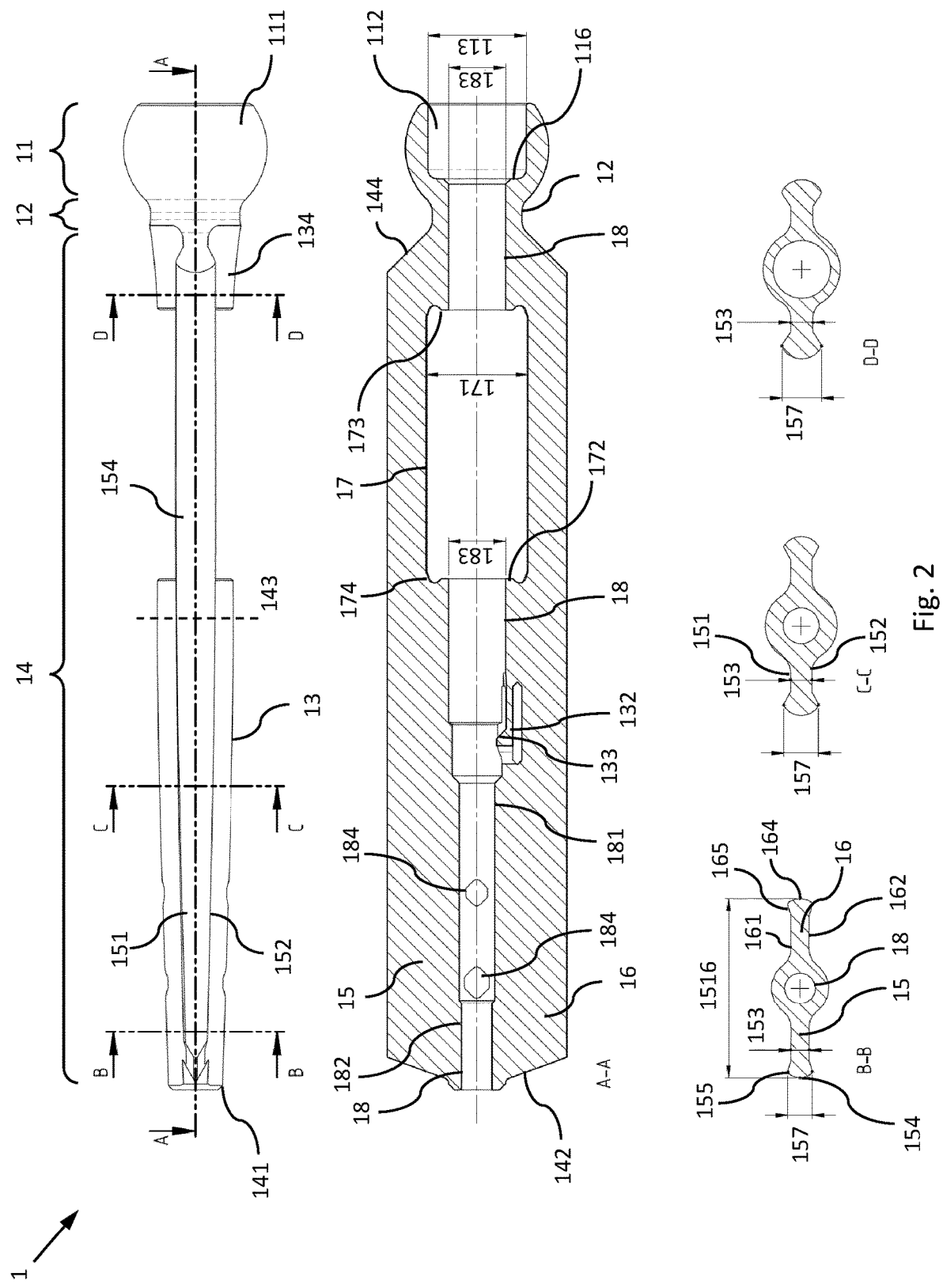

FIG. 2 shows that the bone anchor (1) of the osteosynthesis device (10) has a central and continuous cannula opening (18) with a diameter (183), and in the blade area (14) at least one window (17) with an opening width (171) is provided, and the window (17) interacts with the cannula opening (18), and the head area (11) has an opening (112) with an opening diameter (113), which also interacts with the cannula opening (18). The diameter of the cannula opening (183) is smaller than the opening width of the window (171) and the diameter of the cannula opening (183) is also smaller than the opening diameter at the head (113). Furthermore, it is preferable if the opening width of the window (171) is at least equal to or larger than the opening diameter at the head (113). This applies in particular if threaded bushes with a larger diameter are required. At least one wall section or row of wall sections (116) runs between the opening at the head (112) and the cannula opening (18), connecting the two openings to one another, and these wall sections (116) are located within the head region (11).

The central cannula (18) can be used to accomplish two tasks. On the one hand, the osteosynthesis device (10) according to the invention can be implanted into the bone in a minimally invasive manner guided by a guide wire and, on the other hand, bone cement can be injected through the cannula (18) from proximal. To prevent cement leakage distally, it is preferable if the cannula (18) has at least one tapering (181, 182) in the distal direction (102). The cement can escape into the bone tissue via fenestration openings (184) in the blade area (14). These fenestration openings (184) interact with the cannula (18) and are formed along a secant or surface normal of the wing surfaces (151, 152, 161, 162).

The window (17) provided in the blade area (14) structurally weakens the osteosynthesis device (10), especially in the bending direction. To balance the bending stiffness of the shaft with blade area (14), it is preferable that the wings (15, 16) within the blade area (14) have at least one thickening (155, 165) in sections, which runs mainly parallel to the central axis (103) and increases the bending stiffness of the osteosynthesis device (10). The thickening can be formed as a longitudinal profile along a parallel to the central axis (103) within the wing areas. For example, elongated struts extending along the wings and spaced at any distance from the central axis are possible. FIG. 2 shows a preferred embodiment of the osteosynthesis device (10) according to the invention, in which these thickenings (155, 165) are located at the top edge (154, 164) of the wings (15, 16) and have a greater thickness (157) than the area distance of the wing areas (153). This results in the greatest increase in stability. Furthermore, it is preferable that the top edges (154, 164) have at least one convex curve and that these curves approximate an oval at least in sections. With the approximated oval, the top edges (154, 164) create a homogenized contact zone with reduced contact stresses to the cortical pedicle bone in the cranial-caudal direction. This allows the osteosynthesis device according to the invention to be supported on the cortical pedicle wall and thus better absorb forces.

Since the proximal structures of the osteosynthesis device (10) are subjected to the highest loads during bending, it is advantageous from a mechanical point of view that the thickness (157) of the thickenings (155, 165) at the proximal area (101) is greater than the thickness (157) of the thickenings (155, 165) at the distal area (102). The same applies to the area distance of the wing areas (153) within the blade area. This can also vary along the central axis (103), at least in sections, in order to contribute specifically to the bending stiffness.

It is also advantageous for increasing the bending stiffness of the osteosynthesis device (10) that the core diameter (131) of the shaft (13) increases in the proximal blade area (134) within the blade area (14). It is also beneficial that the blade width (1516) decreases in the proximal blade area (144) and joins the core diameter of the shaft in the neck area (12) to prevent stress peaks at the transition from the blade area (14) to the neck area (12). To reduce stress concentrations in the window area, optional curves or otherwise provided transitions (174) can be provided at the window cutout.

For better insertion into the vertebra, it is advantageous if the distal tip of the blade area has a cutting edge (142) at each wing area, which has either a symmetrical or asymmetrical gate. Optimally, the cutting edge (142) has an acute cutting angle. Orthogonally to this, it is preferable if the cutting edges of both wing areas are at an obtuse angle to each other. It is also desirable if the distal tip (141) of the shaft (13) protrudes in the distal direction. This allows the osteosynthesis device (10) to be guided into a drill channel in the bone with the distal shaft tip (141) as the first contact element. Without this feature, such guidance is more difficult.

Figure 3:
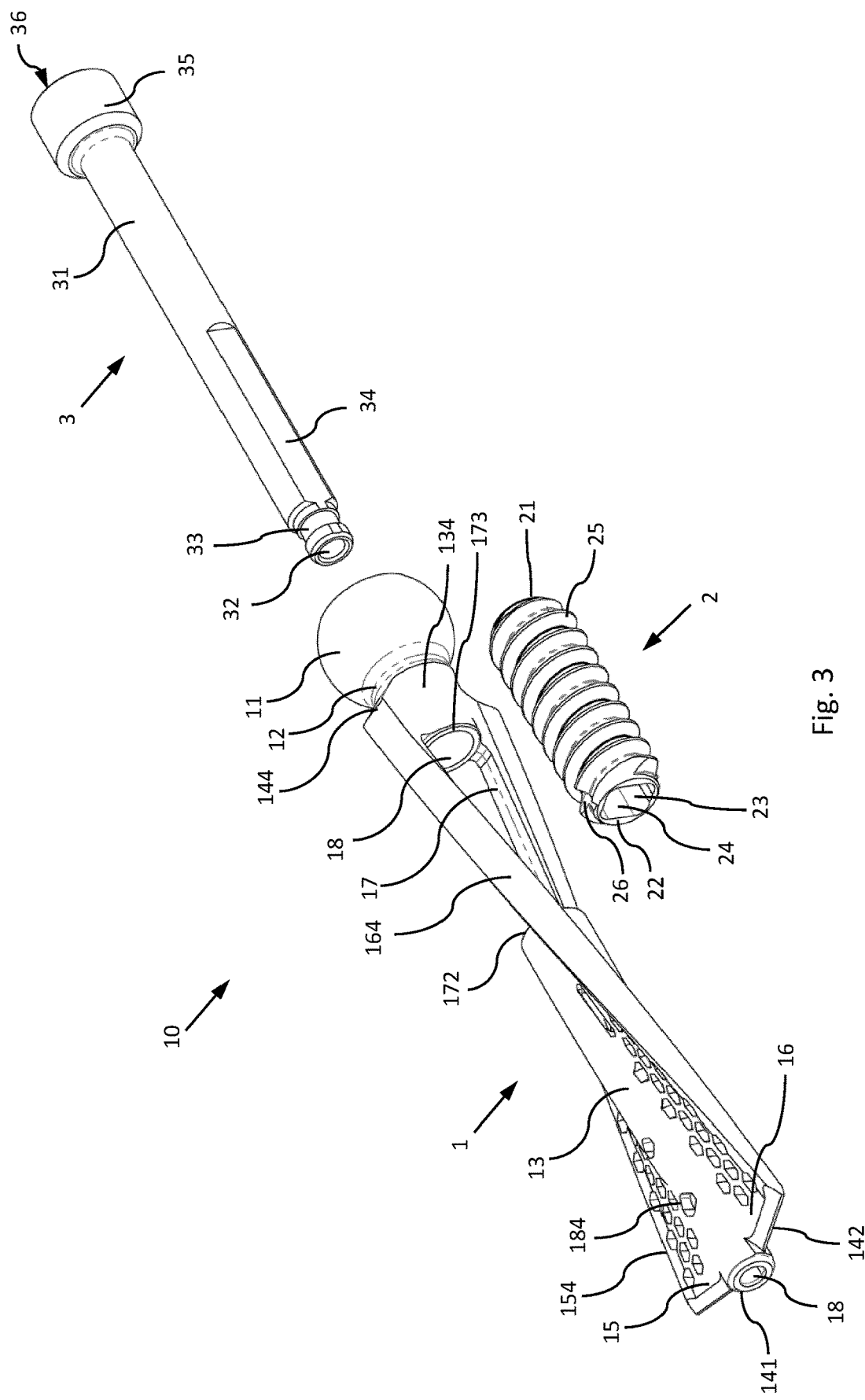

FIG. 3 shows the osteosynthesis device (10) according to the invention with the window (17) and that the window (17) is positioned within the blade area and is closer to the proximal end (144) of the blade area than to the distal end (141) of the blade area (102). A threaded bush (2) having a bone thread (25) is rotatably mounted in the window (17). The bone thread (25) may have at least one cutting edge (26) to provide the thread with a self-tapping property. The position of the window (17) is selected so that the threaded bush (2) is mainly interlocked with the cortical bone in the pedicle region once the osteosynthesis device (10) is fully implanted. The threaded bush (2) has a central opening (23), wherein the diameter of the central opening (23) is approximately equal to the cannula diameter (183) of the shaft (13). This makes it possible for a coupling element (3) to be plugged into the shaft (13) and the threaded bush (2). The coupling element (3) has a head (35) and a tool attachment point (36) therein and an elongated shaft (31). The elongated shaft (31) is supported in the cannula (18) of the shaft (13) and in the threaded bush (2, 23) after being plugged together. Furthermore, it can be seen that the coupling element (3) at the shaft area (31) has in sections at least one profile (34) and the threaded bush (2) has in sections at least one profile (24) congruent therewith, which are in engagement with each other and are suitable for transmitting a torque from the tool attachment point (36) to the threaded bush.

Figure 4:
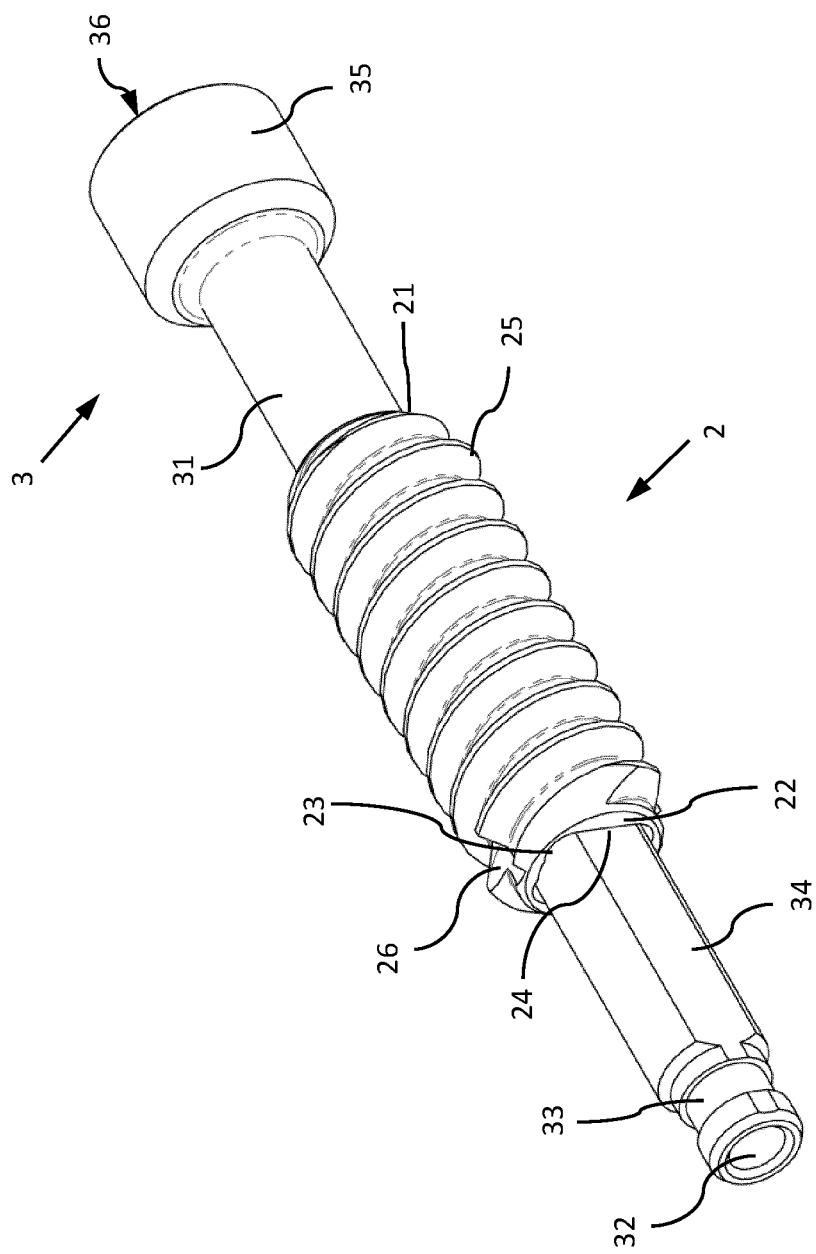
Figure 5:
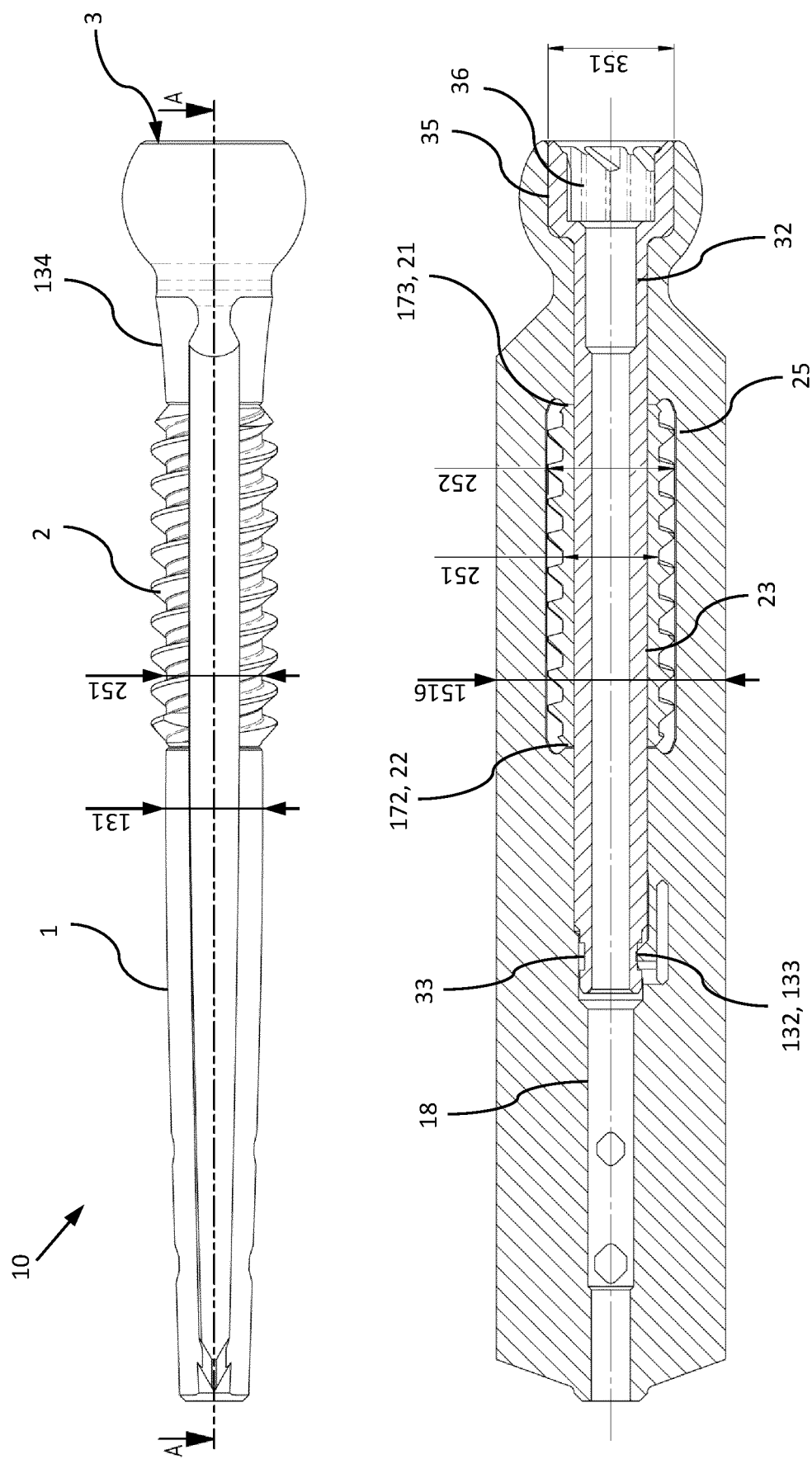

FIG. 4 shows, without the bone anchor (1), how the threaded bush (2) and the coupling element (3) are assembled. An essential feature is that the shaft (31) of the coupling element protrudes distally (102) from the threaded bush (2) and this protruding distal shaft end is supported in the cannula (18) of the shaft (13) of the bone anchor (1). Thus, the shaft (31) has at least two bearing positions within the cannula (18) of the shaft (13), distal and proximal to the threaded bush (2). This allows the coupling element (3) to additionally absorb a bending stress of the shaft (13). As also shown, the coupling element (3) has a cannula opening (32) which interacts with the cannula opening (18) of the shaft (13) in the assembled state (FIG. 5). This is the only way to ensure that the entire osteosynthesis device (10) is cannulated.

FIG. 5 shows that the threaded bush (2) has a distal area (22) and this distal area (22) is in direct contact with a contact surface (172) of the window (17) and this contact serves as a stop. Furthermore, it is shown that the threaded bush (2) has a proximal area (21) and this proximal area (21) is in direct contact with a contact surface (173) of the window (17) and this contact serves as a stop. With these stops, it is possible for the pull-out forces absorbed by the threaded bush (2) to be transmitted to the blade area (14) and then to the bone anchor (1) and finally to the spherical segment (111). Preferably, these stops are designed as concentric planar contact surfaces which simultaneously allow free rotation of the threaded bush (2). Important for the configuration of the osteosynthesis device (10) according to the invention are various dimensional relationships, i. e. that the threaded bush (2) has a thread core diameter (251) which corresponds approximately to the outer diameter of the shaft (131). Furthermore, it must be ensured that the coupling element (3) provides a head (35) and that this head has an outer diameter (351) which is approximately equal to or smaller than the thread outer diameter (252) of the threaded bush (2). Only in this way it is possible to provide a portfolio of osteosynthesis devices (10) with different threaded bush outer diameters (252), which also fit the patient-specific different pedicle sizes. Considering the size variance of the osteosynthesis devices (10), it is preferable if the coupling element (3) as well as the size of the neck area (12) and the head area (11) always remain the same size. Thus, the same tulip heads (4) can be used for adaptation for the different osteosynthesis devices (10). With the variance of the threaded bush outer diameter (252), the size of the blade area must also be adjusted so that the relation of threaded bush outer diameter (252) and blade width (1516) is anatomically consistent. It must be noted that the blade area (14), with the two wings (15, 16) defines a width (1516) between the top edges (154, 164) of the wings, and a thread outer diameter (252) of the threaded bush (2) is defined, wherein the form factor, from the ratio of 1516/252, is between 1.3 to 2.5, preferably 1.4 to 2.2, preferably 1.6 to 2.0.

In FIG. 5, as previously mentioned, it can be seen that the coupling element (3) has a cannula (32) and this cannula (32) interacts with the cannula opening (18) of the shaft (13). Furthermore, a latching mechanism is shown here, in which at least one elastic locking element (132) is provided inside the blade area (14) (FIG. 5) or outside the blade area (115, 11) (FIG. 6), which is latched to the coupling element (3, 33), which on the one hand enables the tool-free assembly of the coupling element (3) and on the other hand provides a retainer of the coupling element (3) in axial direction. Alternatively, but not shown, at least one elastic locking element can also be provided on the coupling element (3), which is latched to the shaft (13) in any way. Latching mechanisms known from the prior art will not be discussed here.

Figure 6:
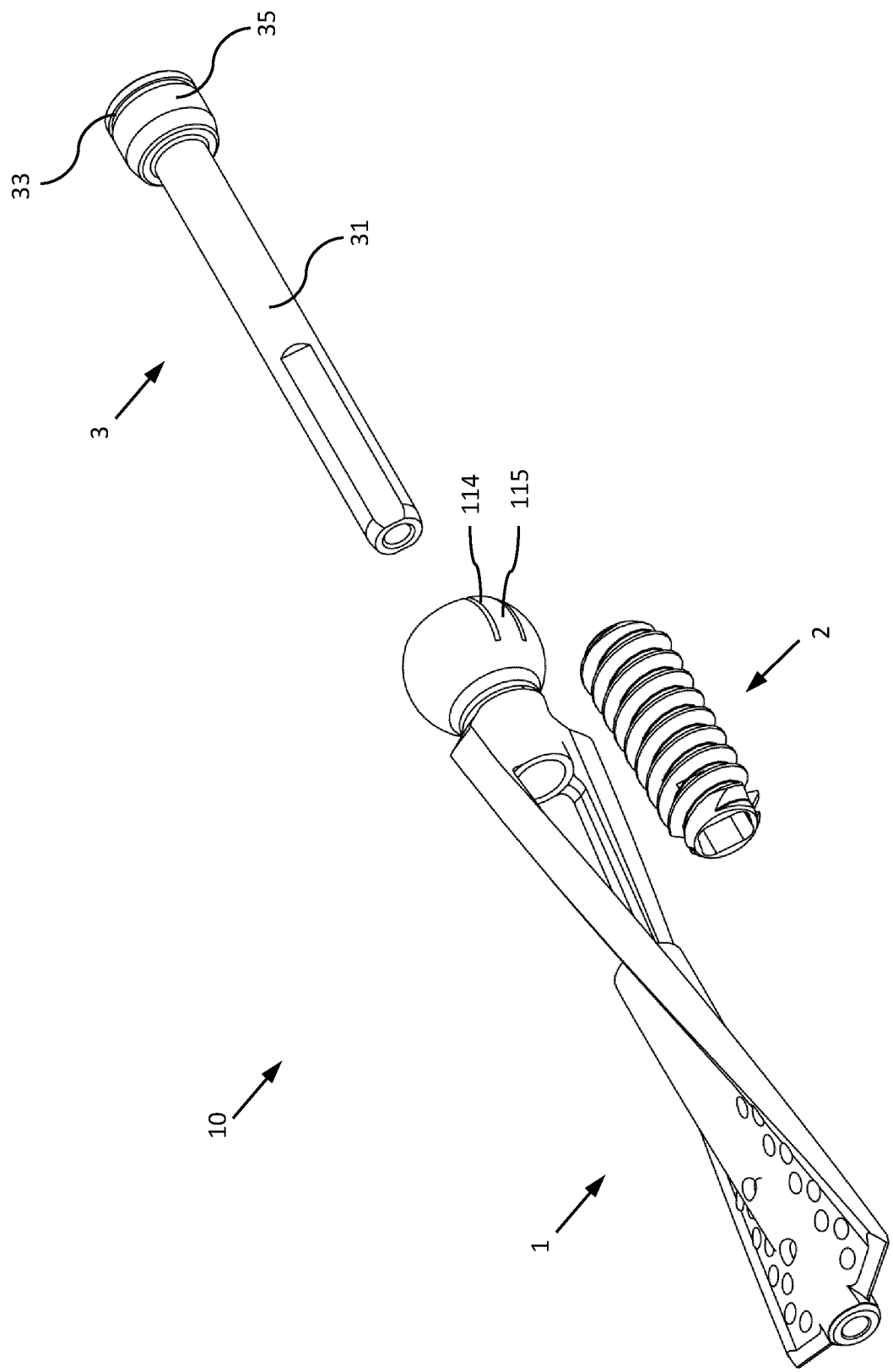

FIG. 6 shows an alternative embodiment of the latching mechanism, wherein the elastic locking element (115) is configured as a spring element which is created by two slots (114). A hook profile is formed on the inside of the elastic locking element (115), which can be latched with a latching groove (33) on the head (35) of the coupling element (3). A converse variant is also possible, in which the elastic locking element is provided on the head (35) of the coupling element (3) and a groove is provided in the head (11).

Figure 7:
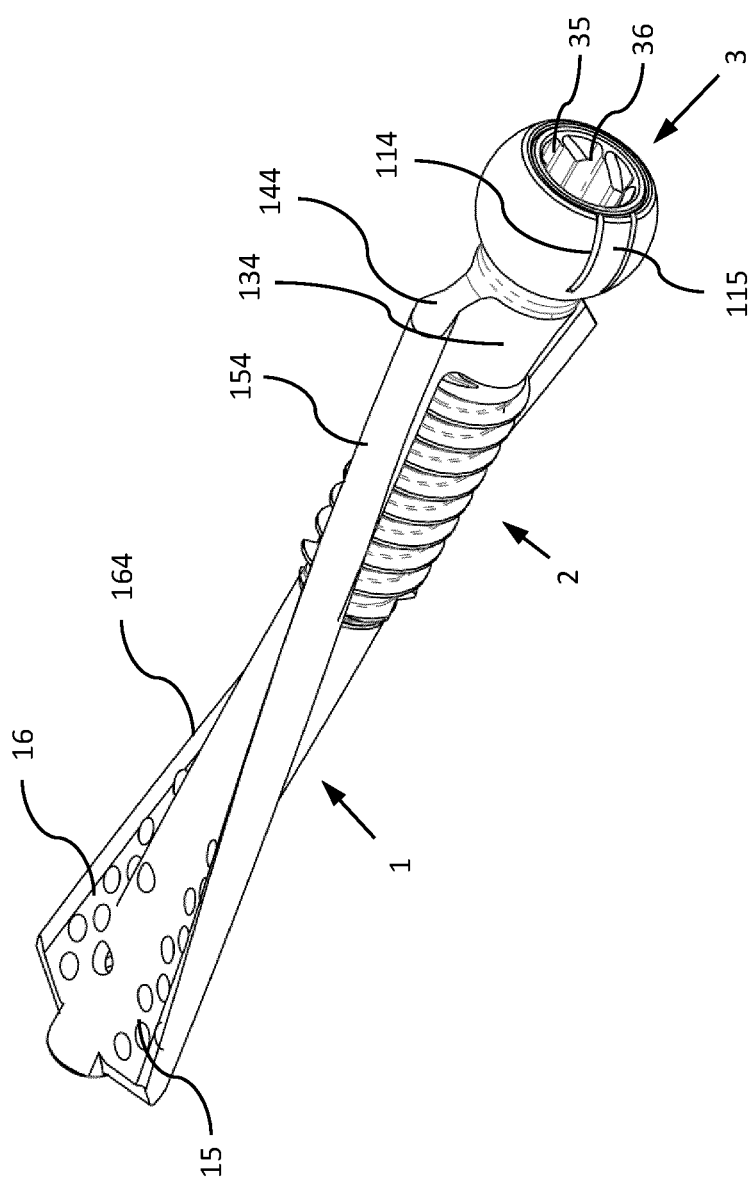

FIG. 7 shows a finally assembled osteosynthesis device (10). The tool attachment point (36), which is provided in the head (35) of the coupling element (3), can be seen. Rotation of the tool attachment point with a suitable instrument forces rotation of the threaded bush (2). Apart from this, the bone anchor (1) is rigid and formed in one piece to provide maximum stability.

Figure 8:
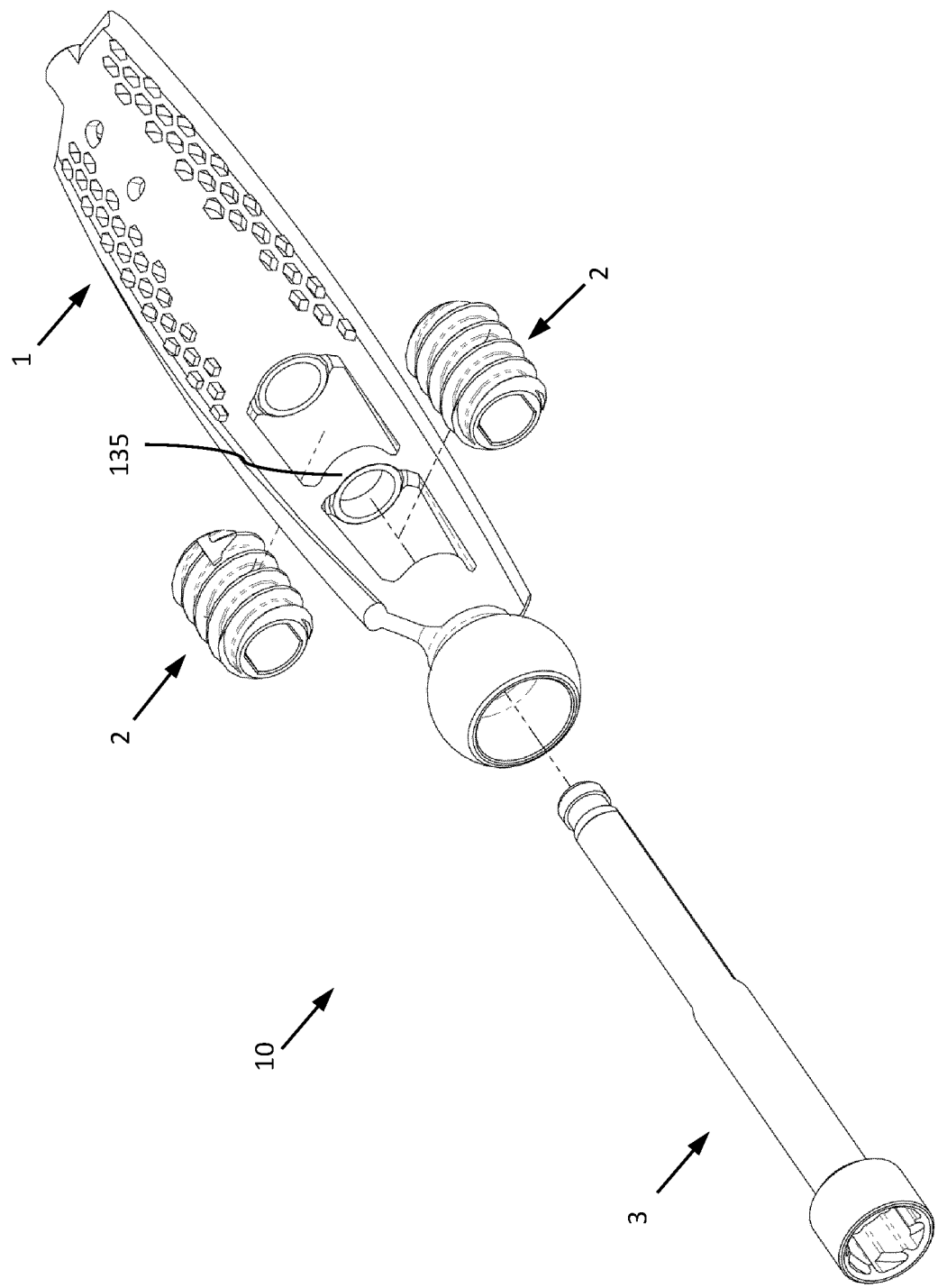

FIG. 8 shows an alternative embodiment in which two threaded bushes (2) are provided which are separated by a bar (135). The width of the bar (135) must be in the factorial range of the thread pitch of the threaded bushes (2) so that the proximal threaded bush runs in the same thread groove during screw-in as the distal threaded bush created during screw-in. The web (135) has the function of providing an additional bearing for the coupling element (3) and thereby increasing the bending stiffness of the bone anchor (1).

Figure 9:
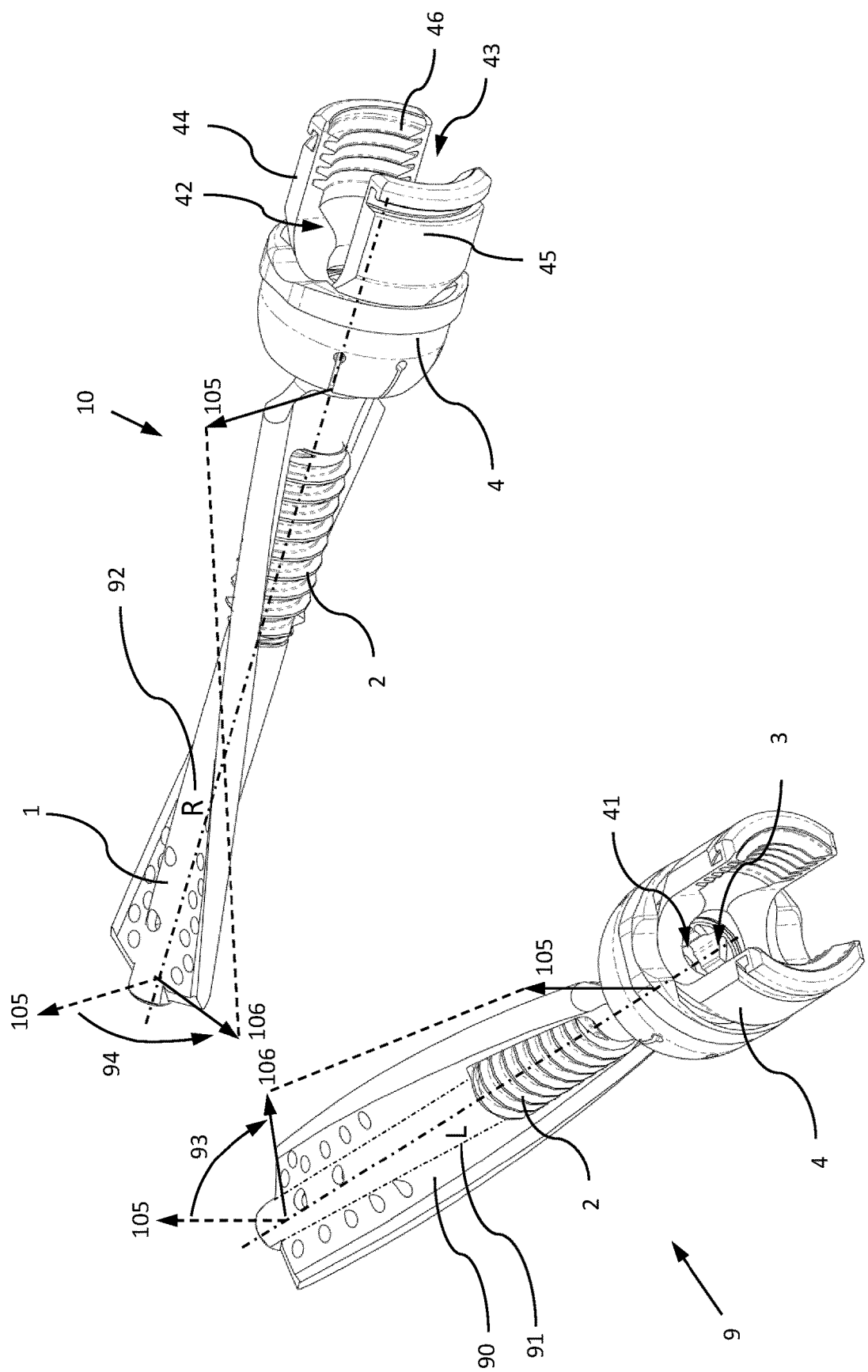
FIG. 9 shows two osteosynthesis devices according to the invention, which have a different orientation of the wing twist.

FIG. 9 shows, as mentioned above, that the osteosynthesis device (10) can be used in combination with a polyaxially swivelling tulip head (4). The polyaxially swivelling tulip head (4) has a u-shaped cutout (42) formed by two legs (44, 45) in side view, which is suitable for receiving a connecting rod (6) and has an internal proximal thread (46) for a fixation element (5).

It was also mentioned at the outset that the pedicle canals have different left and right pedicle profiles in section. It is therefore preferable to provide a left and a right version of a bone anchor (1, 90) in a portfolio of osteosynthesis devices (9, 10). More precisely that means that the blade area (14), with the two wings (15, 16) at the proximal area (101), has a first wing orientation (105) and the wings (15, 16) at the distal end (102) have a second wing orientation (106), which is different from the first wing orientation (105), wherein this difference can be described via a crossing angle (107), and viewed from a proximal direction of view, the crossing is directed against the clockwise direction (94). In addition, the blade area (14) with the two wings (15, 16) at the proximal area (101) has a first wing orientation (105) and the wings (15, 16) at the distal end (102) have a second wing orientation (106) which is different from the first wing orientation (105), this difference being determinable by means of a crossing angle (107), and, viewed from the proximal viewing direction, the crossing is directed in the clockwise direction (93). It is preferable if the osteosynthesis device has a marking or label that provides an indication of the crossing direction or an indication of the anatomic positioning (91, 92). FIG. 9 shows an example of how the different versions are marked with "R" and "L" for right and left (91, 92). Alternative markings or color schemes are also possible.

Figure 10:
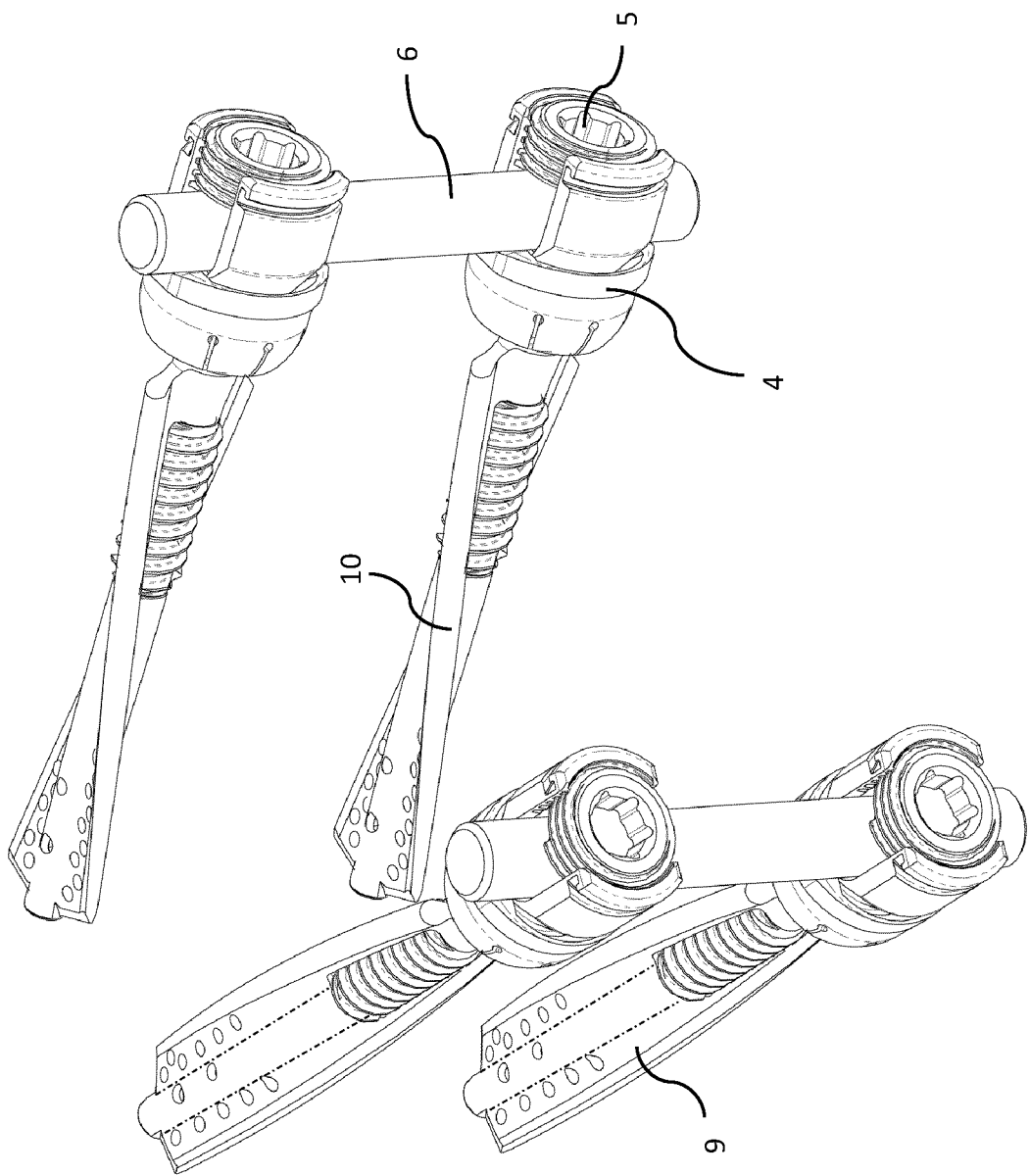
FIG. 10 shows the assembly of different osteosynthesis devices into a construct as used in spinal surgeries.

When assembling a system of at least two osteosynthesis devices (9, 10), it must be noted that at least one of the osteosynthesis devices (9) has a crossing of the wing orientations in the clockwise direction (93) and at least one other osteosynthesis device (10) has a crossing of the wing orientations against the clockwise direction (94) (FIG. 9 and FIG. 10).

The osteosynthesis device can be used in combination with a polyaxial tulip head to allow two or more osteosynthesis devices with tulip head to be assembled together into a rigid construct using connecting rods to stabilize the bony structures (FIG. 10).

The invention claimed is:

1. An osteosynthesis device for the fixation of bone components and bone fragments, comprising:
a bone anchor, wherein the bone anchor has a shaft which extends along a central axis and thereby defines a distal and a proximal direction, and the shaft has a blade area with a first and a second wing, and proximally adjoins a neck area and further has a head with a spherical segment, and
the bone anchor has a central and continuous cannula opening with a diameter, and in the blade area at least one window with an opening width is provided, and
the window interacts with the cannula opening, and a head area has an opening with an opening diameter, which also interacts with the cannula opening, characterized in that the diameter of the cannula opening is smaller than the opening width of the window and the diameter of the cannula opening is also smaller than the opening diameter at the head and the shaft is formed in one piece with the blade area, the neck area and the head with spherical segment,
wherein the opening width of the window is at least equal to or greater than the opening diameter at the head.

2. The osteosynthesis device according to claim 1, wherein the cannula opening has at least one tapering in distal direction.

3. The osteosynthesis device according to claim 1, wherein the shaft has fenestration openings in the blade area that interact with the cannula opening and are formed along a line perpendicular to a surface of the wings.

4. The osteosynthesis device according to claim 1, wherein the wings have at least one thickening in sections which runs mainly parallel to the central axis and increases the bending stiffness of the osteosynthesis device.

5. The osteosynthesis device according to claim 4, wherein the thickening of the wings are located at the top edge of the wings and have a greater thickness than the wings.

6. The osteosynthesis device according to claim 4, wherein the thickness of the thickenings varies along the central axis.

7. The osteosynthesis device according to claim 4, wherein the thickness of the thickenings at a proximal area is greater than the thickness of the thickenings at a distal area.

8. The osteosynthesis device according to claim 1, wherein the outer edges of the wings have a convex curve and this curve approximates an oval at least in sections.

9. The osteosynthesis device according to claim 1, wherein a thickness of the wing varies along the central axis.

10. The osteosynthesis device according to claim 1, wherein within the blade area a core diameter of the shaft increases in a proximal blade area.

11. The osteosynthesis device according to claim 1, wherein a blade width decreases in a proximal blade area and joins a core diameter of the shaft towards the neck area.

12. The osteosynthesis device according to claim 1, wherein a threaded bush with a bone thread is rotationally movably mounted in said window, characterized in that the threaded bush has a central opening.

13. The osteosynthesis device according to claim 12, wherein the diameter of the central opening is approximately equal to a cannula diameter of the shaft.

14. The osteosynthesis device according to claim 12, wherein the threaded bush has a distal area and this distal area is in direct contact with a contact surface of the window and this contact serves as a stop.

15. The osteosynthesis device according to claim 12, wherein the threaded bush has a proximal area and this proximal area is in direct contact with a contact surface of the window and this contact serves as a stop.

16. The osteosynthesis device according to claim 12, wherein the threaded bush has a thread core diameter which is approximately equal to the outer diameter of the shaft.

17. The osteosynthesis device according to claim 12, further comprising a coupling element having a head and a tool attachment point therein, and the coupling element has an elongated shaft, and this shaft is mounted in the cannula opening of the shaft and in the threaded bush.

18. The osteosynthesis device according to claim 17, wherein the coupling element at the shaft has a profile and the threaded bush has a profile congruent therewith, said profiles are in engagement with one another and are suitable for transmitting a torque from a tool attachment point to the threaded bush.

19. The osteosynthesis device according to claim 17, wherein the coupling element is axially insertable into the threaded bush and into the shaft.

20. The osteosynthesis device according to claim 17, wherein a shaft of the coupling element protrudes distally from the threaded bush and the end of this distally protruding shaft is mounted in the cannula opening of the shaft of the bone anchor in the blade area.

21. The osteosynthesis device according to claim 20, wherein the shaft of the coupling element protrudes proximally from the threaded bush and this proximal shaft portion of the coupling element is also mounted in the cannula opening of the shaft.

22. The osteosynthesis device according to claim 17, wherein the coupling element provides a head, said head having an outer diameter which is approximately equal to or smaller than an outer diameter of the thread of the threaded bush.

23. The osteosynthesis device according to claim 17, wherein the coupling element has a cannula and said cannula is connected to the cannula opening of the shaft.

24. The osteosynthesis device according to claim 17, wherein an elastic locking element is provided inside the blade area, which is locked to the coupling element, which on the one hand enables the tool-free assembly of the coupling element and on the other hand provides a retainer of the coupling element in axial direction.

25. The osteosynthesis device according to claim 24, wherein said elastic locking element is provided on the coupling element, which is locked to the shaft.

26. The osteosynthesis device according to claim 12, wherein the blade area, with the two wings defines a width between outer edges of the wings, and an outer diameter of the thread of the threaded bush is defined, wherein the ratio of the width and the outer diameter thread of the threaded bush is between 1.3 to 2.5.

27. The osteosynthesis device according to claim 1, wherein the window is positioned within the blade area and is located closer to a proximal end of the blade area than to a distal end of the blade area.

28. The osteosynthesis device according to claim 1, wherein the osteosynthesis device has a polyaxially pivotable head which in side view has a u-shaped cutout formed by two legs for receiving a connecting rod and an internal proximal thread therein.

29. The osteosynthesis device according to claim 1, wherein the blade area, with the two wings at a proximal area, has a first wing orientation and the wings at a distal end have a second wing orientation which is different from the first wing orientation, this difference being determinable by means of a crossing angle, and, viewed from a proximal viewing direction, the crossing is directed counterclockwise.

30. The osteosynthesis device according to claim 29, wherein the osteosynthesis device has a marking or label providing an indication of the direction of crossing or an indication of anatomic positioning.

31. The osteosynthesis device according to claim 1, wherein the blade area, with the two wings at a proximal area, has a first wing orientation and the wings at a distal end have a second wing orientation which is different from the first wing orientation, this difference being determinable by means of a crossing angle, and, viewed from a proximal viewing direction, the crossing is directed clockwise.

32. A system comprising at least two osteosynthesis devices according to claim 1, wherein a wing orientation of a wing of one of the osteosynthesis devices is twisted clockwise and a wing orientation of a wing of a further osteosynthesis device is twisted counterclockwise.

* * * * *